(12) United States Patent
Belgovskiy et al.

(10) Patent No.: US 7,391,016 B2
(45) Date of Patent: Jun. 24, 2008

(54) METHOD FOR QUANTITATIVE ANALYSIS OF MIXTURES OF COMPOUNDS

(75) Inventors: Alexander Belgovskiy, Mayfield Heights, OH (US); Arnon Chait, Bay Village, OH (US)

(73) Assignee: Analiza, Inc., Cleveland, OH (US)

( * ) Notice: Subject to any disclaimer, the term of this patent is extended or adjusted under 35 U.S.C. 154(b) by 353 days.

(21) Appl. No.: 11/370,326

(22) Filed: Mar. 8, 2006

(65) Prior Publication Data

US 2006/0255257 A1    Nov. 16, 2006

Related U.S. Application Data

(60) Provisional application No. 60/680,317, filed on May 12, 2005.

(51) Int. Cl.
*H01J 49/36* (2006.01)
(52) U.S. Cl. ...................................................... 250/282
(58) Field of Classification Search ............... None
See application file for complete search history.

(56) References Cited

U.S. PATENT DOCUMENTS 6,188,064 B1 * 2/2001 Koster ........................ 250/282
6,717,134 B2 * 4/2004 Bowdler ..................... 250/287
7,071,463 B2 * 7/2006 Bowdler ..................... 250/282

FOREIGN PATENT DOCUMENTS

WO    WO 03/016883 A1    2/2003

* cited by examiner

*Primary Examiner*—David A. Vanore
(74) *Attorney, Agent, or Firm*—Pearne & Gordon LLP

(57) ABSTRACT

The present invention provides for systems and methods for automated quantification of individual compounds in a mixture. The invention is generally concerned with quantitative analysis of solid, liquid, or gas samples and relies on a separation instrument and on a mass detector. The separation instrument provide means to separate the individual compounds typically according to certain physicochemical property, and the mass detector provides means to determine the amount or concentration of an arbitrary compound using an instrument-specific calibration curve. The present invention provides automated capability to analyze such mixtures without user intervention by varying pre-determined control parameters on one or more of the instruments so as to achieve a high degree of analytical resolution of some or all of the individual compounds in the mixture.

14 Claims, 5 Drawing Sheets

Fig. 3

| Line | Vial | Sample Name | Line Type | N Gain | Gain Mode | Opt. Type | Opt. V | Vol. MIN | Vol. MAX | T. Area MIN | T. Area MAX | Rpts | Adv.AZ |
|---|---|---|---|---|---|---|---|---|---|---|---|---|---|
| 1 | 22 | AC 0.025:0.05 | Original | 1 | Auto | Noise-A | ☐ | 0 | 0 | 0.0 | 0.0 | 3 | ☑ |
| 2 | 23 | AC 0.01:1 | Original | 1 | Auto | Noise-A | ☐ | 0 | 0 | 0.0 | 0.0 | 3 | ☑ |
| 3 | 24 | AC 0.1:10 | Original | 1 | Auto | Noise-A | ☐ | 0 | 0 | 0.0 | 0.0 | 3 | ☑ |

Set Columns

| N Gain | Gain Mode | Opt. Type | Opt. V | Vol. MIN | Vol. MAX | T. Area MIN | T. Area MAX | Repeats | Adv.AZ |
|---|---|---|---|---|---|---|---|---|---|
| 50 / 100 | Fixed / Auto | Noise-A / Noise-C | ☐ | 0 | 0 | 0.0 | 0.0 | 0 | ☐ |
| Set | Set | Set | Set | Set | Set | Set | Set | Set | Set |

OK    Cancel

| | A | B | C | D | E | F |
|---|---|---|---|---|---|---|
| 1 | UDS SEQUENCE REPORT | | | | | |
| 2 | | | | | | |
| 3 | Data File | C:\HPCHEM\1\DATA\UDS4\AC7\001-0201.D | | | | |
| 4 | Sample Name | AC 0.025:0.05 | | | | |
| 5 | Seq. Line | 2 | | | | |
| 6 | Location | 1 | | | | |
| 7 | Inj. No. | 1 | | | | |
| 8 | Inj. Vol. | 10 | | | | |
| 9 | Act. Inj. Vol. | 10 | | | | |
| 10 | N Gain | 1019.091 | | | | |
| 11 | Inj. Date/Time | 20-Feb-06, 16:03:38 | | | | |
| 12 | Acq. Method | C:\HPCHEM\1\METHODS\UDS_55M.M | | | | |
| 13 | Analysis Method | C:\HPCHEM\1\METHODS\UDS_55M.M | | | | |
| 14 | Sample Info | Acetaminophen:Caffeine, 0.025:0.05 mg/ml, in water. | | | | |
| 15 | | | | | | |
| 16 | PEAKS | | | | | |
| 17 | | | | | | |
| 18 | RT [min] | Area | Height | UDS_Saturated | UDS_PercentFS | ug/ml N |
| 19 | 5.919571877 | 1508.538 | 96.81012 | 0 | 9.604178535 | 2.69316 |
| 20 | 7.500726223 | 9043.088 | 438.1869 | 0 | 43.47092159 | 14.71533 |
| 21 | | | | | | |
| 22 | END_OF_RUN_DATA | | | | | |
| 23 | | | | | | |
| 24 | Data File | C:\HPCHEM\1\DATA\UDS4\AC7\001-0301.D | | | | |
| 25 | Sample Name | AC 0.025:0.05 | | | | |

METHOD FOR QUANTITATIVE ANALYSIS OF MIXTURES OF COMPOUNDS

This application claims the benefit of U.S. Provisional Patent Application No. 60/680,317 filed May 12, 2005.

FIELD OF INVENTION

The present invention is generally related to the analysis of mixtures of chemical compounds. More particularly, the invention is related to developing methods for quantitative analysis of said mixtures, for example, methods which can directly obtain the concentrations of the individual compounds in a mixture without having to prepare individual standards of such compounds prior to the analysis of the mixture. The invention is of general use in the field of analytical chemistry, for example, for quantification of impurities in a test sample, for analysis of samples following chemical synthesis of organic or other molecules, for stability analysis of chemical compounds or for general analysis of any mixtures containing more than one chemical compound.

BACKGROUND OF THE INVENTION

Analysis of mixtures containing different compounds is typically guided by the information desired. For example, analysis of mixtures of chemical compounds may be directed towards identification of said compounds. A general method to identify mixtures constituents is to first separate the mixture and then use one or more techniques for further identification of the individual compounds. Methods of separation depend on the state of the mixture, solid, liquid, or gas, and on known or assumed characteristics of the compounds in the mixture. For example, chromatography is a well known technique to separate mixture components in the liquid or gas phases based on their mass, size, electrical charge, mobility, affinity to other molecules or other properties.

Once separated, many techniques are available for identification of unknown compounds by probing certain physical or chemical properties. For example, spectrophotometric techniques could be used to identify compounds by comparing their absorption spectra to known spectra. Equally important analysis of mixtures of compounds is related to their absolute quantification. Alone or in tandem with their identification, obtaining information regarding the amounts of mixture components is also important for many analytical applications. For example, it is desired to quantify all chemical compounds in a mixture following synthesis, to monitor transformation of a compound over time or after exposure to other compounds, to quantify only the major component of the mixture, or to quantify minor components such as impurities.

In certain fields, chemical analysis is performed in a high throughput manner, and techniques for rapid identification and quantification of both major and minor components of a mixture are highly desired. For example, modem discovery of organic pharmaceutical compounds involves synthesis and screening of thousands or sometimes millions of chemical compounds. Since synthesis techniques are never perfect, compounds that demonstrate initial biological activity are then sent to further chemical analysis. Such analysis involves separation of the assumed mixture of compounds, quantification and identification of all of the constituents. This information could then be used to assess properties of the mixture, such as biological activity, physicochemical parameters such as solubility and lipophilicity and other information relevant to the use of the compound.

While identification of the individual compounds in a mixture can deploy many techniques which probe the chemical composition using multiple physical and chemical aspects, techniques for quantification of said compounds are much more limited in number and scope. Most generally, the compounds in a mixture must be separated and identified. Once separated and identified, standards of the individual components containing known amounts of the mixture are prepared. These standards are typically subjected to further analyses correlating certain physical or chemical properties to their a priori known amounts thus constructing a calibration curve. Finally, the unknown amounts of the components in the mixture are calculated from measuring the same properties previously measured from the standards and using the calibration curve in reverse.

Preparing standards, developing individual calibration curves, and quantifying unknown compounds is a highly resource and time consuming process and not suitable for high throughput analyses. A significant simplification of this process could be achieved if calibration curves could be constructed for a large class of chemical compounds based on a common attribute that could be directly measured. For example, equimolar elemental techniques produce signals which are proportional to the amount of an individual element in the sample. Detectors for quantifying the total carbon, nitrogen or other elements are available. Usually standards containing known amounts of such elements are used to construct calibration curves, which could then be used to analyze any compound containing such elements without the need to prepare an individual series of standards for each unknown compound. In a common scenario, the compound is provided in known volume to the detector which then produces a signal that is proportional to the amount of the element in the sample, thus directly producing a quantitative measure as a total mass or, for example, as parts-per-million or milligrams per milliliter when considering the known volume and properties of the solvent phase. Once the compound is identified, its amount or concentration could be calculated using the number of atoms in the molecule and its molecular weight, for example.

Elemental detectors could achieve an intrinsically very large dynamic range, e.g., from part-per-million to percent concentration of the analyte. However, due to the much more limited range of certain internal components of the detector, for example, a photo-multiplier tube, the overall large dynamic range is realized using sensitivity level selectors. When these detectors are connected to an upstream separation system, a potentially powerful quantification system is possible. For example, a liquid solution containing a mixture of unknown compounds could be injected into a high performance liquid chromatography system which separates the mixture based on any desired property. The eluent from the chromatography column could be directly diverted into an elemental detector and each of the unknown constituent compounds could be quantified and converted to any convenient concentration unit.

In practice, such combination still necessitate constant manual intervention by the analyst, since in most typical applications, the interest is in quantifying a major component in the mixture simultaneously with much smaller amounts of minor components, sometime referred to as impurities. The analyst has to inspect the analysis signal, select alternative sensitivity settings, and repeat the analysis to optimize the signal to noise ratio for each and every desired separated compound. Thus while the entire process is still much simplified, requiring no individual calibration curves to be constructed, the analysis is still cumbersome and requires attention and interim signal evaluation by a trained analyst in order to optimally quantify each component in the mixture.

Devising an automated process which combines both separation and elemental quantification systems, together with a signal analysis and sensitivity gain optimization and control program, is highly desirable, especially for unattended high throughput analyses of mixtures.

SUMMARY OF THE INVENTION

This invention is generally related to quantitative analysis of mixtures containing multiple chemical species and/or compounds. Specifically, the analysis is aimed at determining the total amount or concentration of individual compounds in the mixture without providing standards and/or individual calibration curves.

In one embodiment, a mixture containing one or more compounds in the solid, liquid, or gas states is subjected to the methods described in the present invention to determine the individual amounts or concentration of its constituents. The method presented herein further provides for such determinations in both cases when the individual chemical identity and/or composition of the compounds are known or not. Furthermore, the method provides for automated processing and determination of all amounts or concentrations of the compounds in the mixture without user intervention.

In another embodiment, the method of the present invention describes a combination of software and/or hardware for automated analysis and control of separation and detection instruments. Such combination provides for optimization of the signal obtained for each compound to enable high resolution quantification regardless of the absolute quantity of each compound in the mixture.

Other advantages and novel features of the invention will become apparent from the following detailed description of various non-limiting embodiments of the invention when considered in conjunction with the accompanying figures. In cases where the present specification and a document incorporated by reference include conflicting disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures:

FIG. 3. Sequence table in ChemStation (Agilent) representing the initial user-provided input for analyzing three sample mixtures.

FIG. 4. Sequence table following the automated analysis, with extra sequence lines corresponding to additional sample injections and analyses as determined by a peak optimization algorithm according to the methods of the present invention.

FIG. 5. Automated analysis of results, based on a calibration table data and run results, in parts-per-million of nitrogen and in weight per volume concentration units.

DETAILED DESCRIPTION

Incorporated Documents

Figure 1:
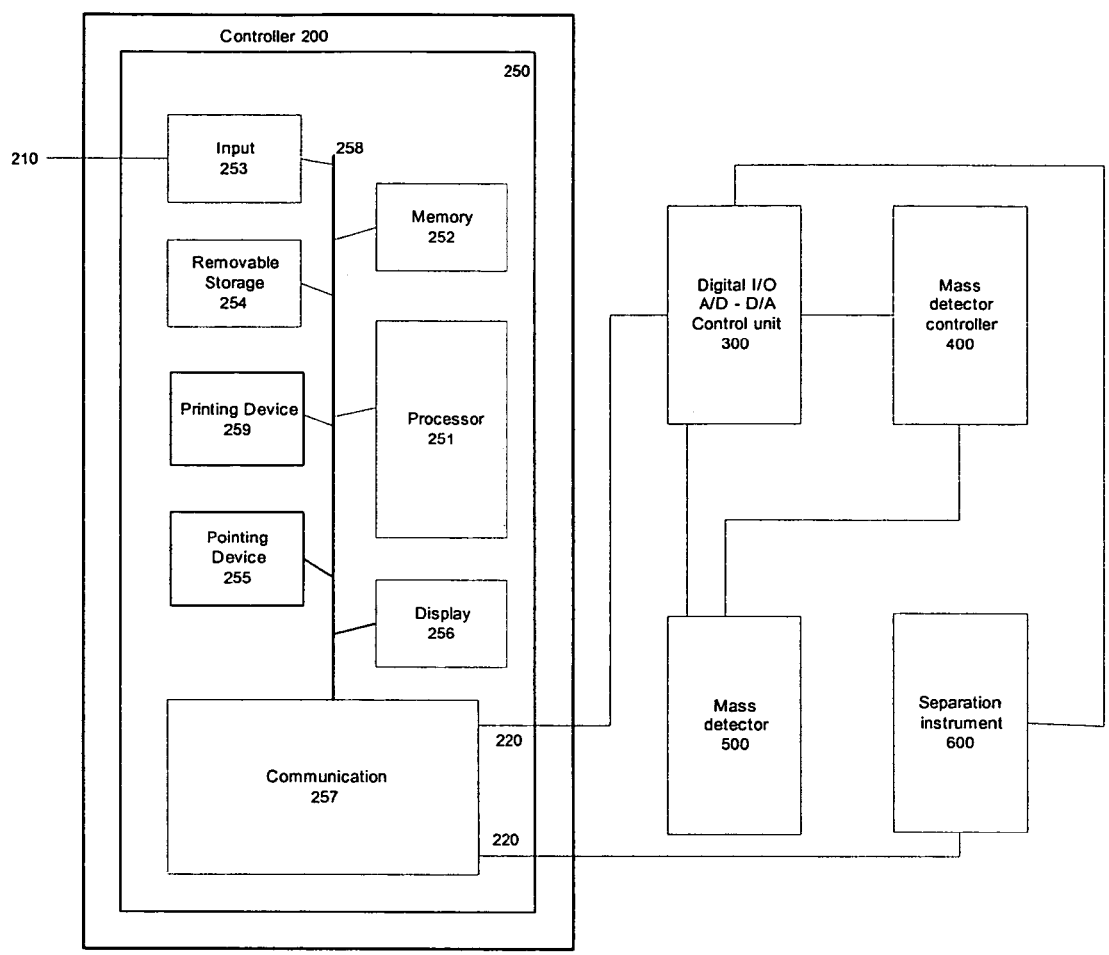
FIG. 1. Schematic of a system combining separation and mass detector instruments and controller with other devices according to the present invention.

The following document is incorporated herein by reference in its entirety: WO 03/016883 A1 published Feb. 27, 2003, filed as International application number PCT/US02/26019 (Aug. 16, 2002), entitled "A Method for Measuring Solubility," by Chait et al.

Selected Definitions

As used in the specification and the appended claims, the singular forms "a," "an" and "the" include plural referents unless the context clearly dictates otherwise. Thus, for example, reference to "a biomolecule" can include mixtures of a biomolecule, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, "or" is understood to mean inclusively or, i.e., the inclusion of at least one, but including more than one, of a number or list of elements. Only terms clearly indicated to the contrary, such as "exclusively or" or "exactly one of," will refer to the inclusion of exactly one element of a number or list of elements.

"Optional" or "optionally" means that the subsequently described event or circumstance may or may not occur, and that the description includes instances where said event or circumstance occurs and instances where it does not.

"Analyte," "analyte molecule," "compound," "chemical compound," or "analyte species" refers to a molecule whose amount or concentration are to be determined. "Mass detector," "equimolar detector," "elemental detector," and "light scattering detector" refer to an instrument capable of directly measuring the amount or concentration of an unknown compound without requiring a compound-specific calibration to be constructed ahead.

"Calibration curve" refers to an input-output relation of an instrument, for example, the voltage signal level corresponding to a known amount of compound that is introduced into the instrument.

"Automatic" or "automatically" refers to operational sequence of instruments that is performed without explicit user intervention. As used in the present invention, automated operation includes the combination of automatically performing a quantification of a sample, analyzing the results, changing or selecting different instrument settings, and repeating the quantification to achieve results that provide certain additional benefits or advantages such as accuracy.

"Signal" refers to the output from an instrument, for example, voltage, which corresponds to an input to the instrument, for example, a sample. Typically, a signal will vary over time.

"Signal level" refers to a characteristic of the signal, for example, its maximum height, its integral, width, or other shape characteristics.

"Peak" refers to an output signal region from the detector that deviates from the baseline signal by more than a predefined experimental noise level.

"Saturated peak" refers to an output signal region that exceeded the maximum detector output and is therefore electronically clipped.

"Run" or "instrument run" refer to a completed experimental processing of a specific sample, typically including introduction into the experimental system and acquisition of the response signal from the system.

"Control and analysis system" refers to a combination of hardware and software with capabilities to acquire a signal, analyze said signal, and modify certain operational parameters of the instrument that produced said signal.

Embodiments

When a mixture is analyzed for the quantitative amount or concentration of its constituent compounds, an advantageous combination of instruments is available. Depending on the origin and availability of the mixture, a sample in the solid, liquid, or gas phase could be separated using standard analytical separation techniques such as chromatography. For example, gas chromatography and high performance liquid chromatography could be used to separate mixtures in the gas or liquid states, respectively.

Once separated, many on-line detectors are available for analysis of the separated components. These include UV-VIS absorbance spectra, fluorescence spectra, etc. While these detectors are highly versatile for qualitative analysis of the mixture, quantification of the individually separated compounds must rely on additional information. Such information allows the conversion of the measured signal, e.g., absorbance at a particular wavelength, into the desired quantity units, e.g. concentration. Unfortunately, such conversion necessitates an a priori knowledge of the compound identity, and also a specifically constructed calibration curve using standards, if the particular relationship of between the measured signal and its quantity is unknown as is typically the case. This latter step is highly—time and—resource consuming, and presents a significant obstacle for high throughput automated quantification of arbitrary mixtures, such as those obtained in combinatorial libraries of organic compounds.

Elemental or light scattering detectors provide a way to quantitate a compound without requiring constructing a compound-specific calibration curve. A common attribute of these detectors is that a calibration curve is constructed against the specific parameter being measured, for example, the number of nitrogen atoms being measured. Thus, it is easy to determine the total number of nitrogen atoms by integrating the signal vs. time of the sample introduced to the detector. It is likewise easy to determine the concentration in, e.g., weight per volume, if the sample is introduced in known volume, e.g., via a sampling loop.

Connecting separation and equimolar, elemental or light scattering instruments provides for powerful capabilities to quantitate mixtures in single step without requiring individual standards. However, present day integration of such instruments still necessitates manual intervention to optimize the signal properties of each individual compound in the mixture, especially if there is a large disparity in the amounts or concentrations of the mixture constituents. Every detector has an inherent limitation in the dynamic range of signal that could be processed with acceptable precision. To increase the detector capability to work with a mixture containing large disparity in the amounts of its constituent compound, adjustments of the gain or inherent instrument sensitivity are made. These adjustments must be done after examining the properties of the signal acquired by the instrument. For example, if the signal magnitude is small, the sample must be re-introduced to the detector after its gain is increased to allow for a larger response to be measured. For samples containing a major and several minor compounds, multiple sample introductions and gain re-settings must be performed before full quantification of the mixture is made. This process is time consuming and typically necessitates expert evaluation of each signal to estimate the next gain to be used by the instrument. Thus, a technique is desired to enable signal acquisition, analysis, and instrument control to automatically optimize the signal response of each compound without requiring user intervention.

According to one aspect of the present invention, a computer and/or an automated system is provided able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. One specific example of a technique that can make use of a computer or other automated system is in a process in which certain properties of an electronic signal obtained from a mass detector are used to determine if it provides for adequate determination of the amount or concentration of the compound. If the signal is not capable to adequately resolve the amount or concentration, the process then deploys an optimization strategy, in which certain instrument parameters are controlled and changed to provide better resolution in subsequent sample introduction. When the process is used to control the separation instrument as well as the mass detector, a fully automated operation is possible, in which certain parameters of both instruments can be varied to resolve some or all of the compounds in the mixture automatically without user intervention.

FIG. 1 is a schematic block diagram of an example system according to one embodiment of the present invention. In the embodiment illustrated in FIG. 1, a controller 200 is implemented on a conventional personal computer 250 that includes a processor 251, a memory 252, an input device 253, optionally a removable storage device 254, a pointing device 255, optionally a printing device 259 (such as a printer), a display device 256, and a communication device 257, all coupled together via a bus 258. In a conventional manner, memory 252 may include a variety of memory devices, such as hard disk drives or optical disk drives, RAM, ROM, or other memory devices and combinations thereof, and input device 253 may include a keyboard, a microphone, or any other form of input device capable of receiving one or more inputs 210 from a user of controller 200. Removable storage device 254 may include a CD-ROM drive, a tape drive, a diskette drive, etc. and may be used to load application software, including software to implement various embodiments of the present invention described herein. Display 256 may include a conventional CRT display screen, a flat panel display screen, or any other type of display device that allows textual and graphical information to be displayed to the user, and pointing device 255 may include a puck, a joystick, a trackball, a mouse, or any other type of pointing device or scrolling device that permits the user to select from among the various textual information displayed on the display device 256. Communication device 257 may include any form of communication transceiver capable of receiving one or more inputs 220 from an optional intermediate digital control and data acquisition system 300 which is connected to an optional mass detector control system 400, to a mass detector 500, and to a separation instrument 600, and providing one or more outputs to the same. FIG. 1 illustrates, without loss of generality, one such communication and control hardware arrangement. For example, communication device 257 may include a RS232/485 communication transceiver, a 4-20 mA analog transceiver, an Ethernet transceiver, etc. The separation instrument 600 may be, for example, a gas chromatograph or a liquid chromatograph such as a high performance liquid chromatograph. The mass detector 500 may be, for example, a light scattering instrument (such as an evaporative light scattering detector), a total elemental detector, a total carbon detector, a total nitrogen detector, or a total sulfur detector.

Software, including code that implements embodiments of the present invention, may be stored on some type of removable storage media such as a CD-ROM, tape, or diskette, or other computer readable medium appropriate for the implemented memory 252 and the removable storage device 254. The software can be copied to a permanent form of storage media on the computer 250 (e.g., a hard disk) to preserve the removable storage media for back-up purposes. It should be appreciated that in use, the software is generally and at least partially stored in RAM, and is executed on the processor 251.

Various embodiments of the present invention can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present invention are described in terms of a general purpose computer, it should be appreciated that the use of a general purpose computer is exemplary only, as other configurations may be used.

As shown in FIG. 1, the controller 200 is adapted to be coupled to an optional intermediate digital control and data acquisition system 300 which is connected to an optional mass detector control system 400, to the mass detector 500, and to a separation instrument 600 to analyze the data obtained from such instruments and to control their operations. Controller 200 includes an input 210 to receive one or more parameters from a user of the controller 200 relating to the desired operation to be performed. The controller 200 also includes a plurality of inputs 220 to receive signals relating to the operational status of the mass detector and separation instrument apparatus, and a plurality of outputs 220 to configure and control the same. User input parameters received on input 210 may general assay setup for the separation and mass detector instruments, details concerning the analysis and preferred optimization modes of varying parameters of both instruments, reporting of the results, etc.

Some embodiments of the present invention permit the user to specify one or a number of input parameters relating to the operation of the separation and mass detector instruments, and then, based upon the input parameters, to configure and control said instrument. Depending upon the number of input parameters specified by the user, the controller may prompt the user for additional parameters prior to configuring the instruments.

In the system diagram illustrated in FIG. 1, a master control program resides in the memory 252 which is typically used to control and analyze the separation instrument. The memory 252 also contains additional control programs that interact specifically with the mass detector. The various components are connected as illustrated in FIG. 1 to accommodate specific designs and signal forms of the two instruments and could be substituted by other means to achieve the same control and analysis functionality. In particular, the additional control and optimization program which automates the processing parameters of both instruments 500 and 600 resides in 252 and is executed by the computer 250.

According to another embodiment of the present invention, controller 200 may include a database and/or a knowledgebase that can be accessed by processor 251. According to one embodiment of the present invention, the database may include a plurality of records, each record corresponding to a particular set of parameters for which both instruments 500 and 600 may be used to separate and quantitate the signal corresponding to the separated mixture. In general, each of the records stored in the database reflects empirical data based upon use of the instruments 500 and 600 under defined conditions, or the use of apparatus under defined conditions. The controller 200 and the database may thus be viewed as forming an "expert" system. The database may be stored on a removable storage medium and copied to memory 252 for use by the processor 251, or alternatively, the controller may be pre-configured to include the database.

The following examples are set forth so as to provide those of ordinary skill in the art with a complete disclosure and description of examples of how the compounds, compositions, articles, devices and/or methods claimed herein are made and evaluated, are intended to be purely exemplary of the invention, and are not intended to limit the scope of what is to be regarded as the complete invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. The following examples are intended to illustrate certain aspects of certain embodiments of the present invention, but do not exemplify the full scope of the invention.

EXAMPLE 1

This example illustrates a particular hardware and software arrangement used to provide automatic parameter control as to optimize the quantification of components of a mixture of compounds.

A digital computer 250 (Model No. DHM from DELL, Austin, Tex.) with associated processor, memory, input/output, pointing device, printing device, display and communications was used as the controller 200. The mass detector 500 was a total nitrogen detector model 8060 (Antek Instruments, Houston, Tex.), and the separation instrument 600 was a high performance liquid chromatography system model 1100 (Agilent Technologies, Palo Alto, Calif.). A dedicated mass detector controller 400 was used to change the mass detector gain controls (sensitivity levels) (ANALIZA, Cleveland, Ohio), and the general input/output and analog-digital, digital-analog and control functions unit 300 was model 35900E ADC (Agilent). The software controlling the separation, data analysis, and reporting was Chemstation (Agilent), and the mass detector controller software was written in LabView (National Instruments, Austin, Tex.) by ANALIZA. The parameter optimization module was written using Chemstation macro language.

EXAMPLE 2

This example illustrates a particular software configuration for acquisition and storage of a universal calibration curve for nitrogen containing compounds under Chemstation.

Figure 2:
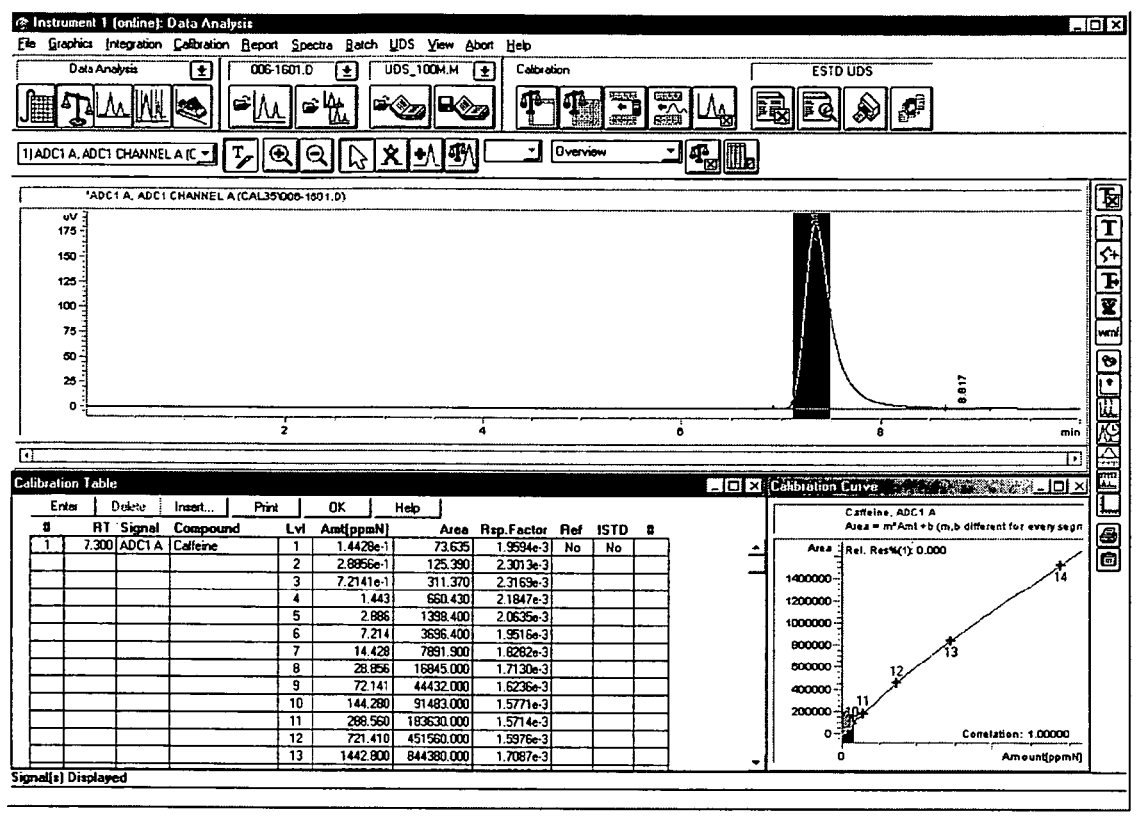
FIG. 2. Construction of a mass detector calibration curve within the Chemstation software (Agilent) of the 8060 total nitrogen detector (Antek).

FIG. 2 illustrates using a screen shot from the Chemstation software of a calibration curve comprised of injections of caffeine, extending over 4 orders of magnitude in concentration. The constant volume injections of 5 ul using 99.99% MeOH and 0.01% HCOOH as a mobile phase were automatically optimized using an automated macro algorithm written in Chemstation which is described in Example 3. The calibration curve was then stored for later use with mixtures of unknown compounds.

EXAMPLE 3

This example illustrates how an optimization algorithm could be used to vary the instruments parameters to achieve high resolution of quantification of each of the compounds in the mixture.

FIG. 3 illustrates the performance of one optimization algorithm for quantification of mixtures prepared from acetaminophen and caffeine, in the following proportions:

| Sample Name | Acetaminophen, mg/ml | Caffeine, mg/ml | Acetaminophen, ppm N | Caffeine, ppm N |
|---|---|---|---|---|
| AC 0.025:0.05 | 0.0250 | 0.050 | 2.316 | 14.428 |
| AC 0.01:1 | 0.0083 | 0.833 | 0.772 | 240.47 |
| AC 0.1:10 | 0.0980 | 9.804 | 9.084 | 2829.0 |

The samples were injected into the 1100 HPLC (separation instrument 600), quantified using the Antek 8060 (mass detector 500), and the results analyzed using the optimization algorithm described below which was executed on the computer 250 within the Chemstation analysis and control software. The optimization algorithm was designed to perform the following steps:

1. Begin with the lowest mass detector sensitivity gain.
2. Inject sample into the separation instrument and analyze eluent stream using the mass detector.
3. Electronically capture the output analog signal from the separation instrument, convert to digital signal, and send back to control and analysis unit.
4. Identify peaks and mark saturated peaks in the report.
5. Define signal region(s) in the chromatogram outside of peaks detected in (2).
6. If the current mass detector gain is Gmax (the maximal gain setting), then go to (7).
7. Calculate next mass detector gain as Gnext<=Gprev× (Vmax ADC)/Vmaxout, where Vmaxout is maximum voltage height in the region defined in (4) and Vmax ADC is the maximum input voltage to the ADC unit 300.
8. Re-inject samples, go to (2).
9. (Optional) Increase the injection volume, re-inject at maximum G=5000,
10. Quantify some or all peaks in the region(s) which found in (4).

Figure 4:
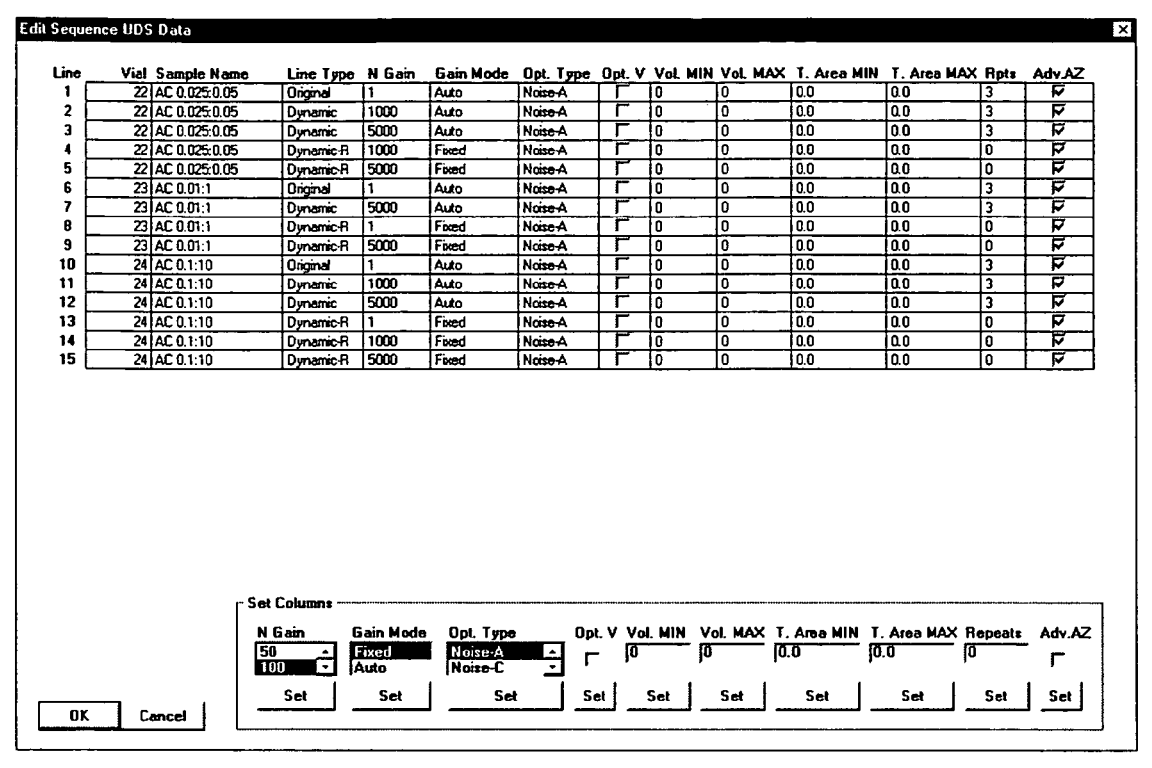

The above process was implemented in ChemStation (Agilent) macro language and is illustrated in the following Figures. FIG. 3 shows the user input (210) to the program, herein referred to as the run sequence table, requesting processing of the three samples in the above table, selecting certain choices of optimization algorithms as described herein, and further requesting repeats of the samples to be quantified. Following complete automated run of such samples, the same sequent table is shown in FIG. 4, where it is evident that additional sequence lines (sample injections) were automatically inserted by the program based on analysis of the mass detector signal at each step. For example, the first sample injection with initial mass detector gain of 1 resulted in the generation of two additional lines, with gains of 1000 and 5000, respectively, as well as two additional injections of the same gains as repeats. The optimization algorithm has caused the gain to automatically change from 1 to 1000 in a single step, based on the evaluated properties of the signal according to the algorithm herein. However, re-injection of the sample to acquire repeats used the already optimized gain parameters; thus, the first gain setting of 1 was not repeated since it did not result in an adequately resolved peak, whereas the two gains of 1000 and 5000 were repeated. The process furthermore was repeated with the additional samples requested by the user in the original sequence table setup.

In the present example, results from all of the sample injections were subsequently converted to an Excel (Microsoft, Redmond, Wash.) format (see FIG. 5), and analyzed using automated procedures implemented in Excel macro language. In this case, the calibration curve of the mass detector was imported to the Excel program, as well as the run results. A simple piece-wise linear interpolation, well known to those skilled in the art, was used to calculate the sample concentration in parts-per-million first, and then, optionally using known molecular weight and number of nitrogen atoms per molecules, convert to mass per volume concentration units. Without the loss of generality, different concentration units may be used, depending on the specific type of mass detector employed.

Yet another optimization algorithm can be designed to reduce or eliminate the number of injections (step 8) in the above algorithm. For example, the rate of change in the signal can be monitored by the system, and the gain can be instantaneously modified according to a pre-determined protocol, such that the output signal from the mass detector will not exceed the maximum allowable limit, yet will be sufficiently greater than the background noise. The instantaneous gain setting and corresponding signal are tracked by the system, and are used during subsequent calculations to determine the instantaneous mass readings by the detector. In one embodiment, the above algorithm is implemented according to the following steps:

1. Begin with the lowest mass detector sensitivity gain.
2. Inject sample into the separation instrument and analyze eluent stream using the mass detector.
3. Electronically capture the output analog signal from the separation instrument, convert to digital signal, and send back to control and analysis unit.
4. For signal levels that are above the average noise level in a pre-determined amount, calculate the time rate of change of the signal.
5. Optionally determine a moving average of the time rate of change of the signal over a pre-determined time interval.
6. Compare the instantaneous or moving average time rate of change of the signal with pre-determined limits. If the values are lower than the low limit, increase the mass detector gain. If the values are higher than the high limit, decrease the mass detector gain.
7. Record the instantaneous signal level and corresponding gain setting.

8. Divide the signal by the corresponding gain.
9. Integrate the quotient of step 8 over the individual peak regions.
10. For each peak, use the calibration curve or table to calculate the concentration using the integral obtained in step 9.

Without a loss of generality, the first algorithm above resulted in optimal resolution and quantification of all identified peaks with a minimum number of injections. Other algorithms may be designed, depending on the particular design of the separation instrument and mass detector, the number of parameters to be optimized and other software design considerations. In particular, algorithms may reside on multiple instruments and software programs such that the entire operational performance of the present invention is accomplished. The control parameters in the optimization algorithm can include varying the sensitivity gain settings of the mass detector, varying the injection volume of the separation instrument, and varying the mobile phase gradient of a high performance liquid chromatograph. Also, the optimization algorithm can be used to modify the signal characteristics in a subsequent instrument run following the conclusion of signal acquisition in a prior run, and can be used to modify the signal characteristics during the instrument run. The optimization algorithm can be provided so that it automatically changes at least one, two, three, four, five, six or more pre-defined individual instrument parameters so as to optimize at least one, two, three, four, five, six or more signal characteristics of at least one, two, three, four, five, six or more peaks in the signal that correspond to at least one, two, three, four, five, six or more constituent compounds in the mixture. The quantity or concentration of at least two, three, four, five, six or more constituent compounds in the mixture can be calculated by converting their corresponding peak signal levels using the mass detector calibration curve.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention.

The definitions, as used herein, should be understood to control over dictionary definitions, definitions in documents incorporated by reference, and/or ordinary meanings of the defined terms.

It should also be understood that, unless clearly indicated to the contrary, in any methods claimed herein that include more than one act, the order of the acts of the method is not necessarily limited to the order in which the acts of the method are recited.

In the claims (as well as in the specification above), all transitional phrases such as "comprising," "including," "carrying," "having," "containing," "involving," and the like are to be understood to be open-ended, i.e. to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for automated quantification of at least 2 constituent compounds in a mixture without requiring individual calibration curves for each constituent compound, comprising the steps of:
   a. providing a separation instrument, a mass detector, and a control and analysis system;
   b. constructing a calibration curve of the mass detector and storing said calibration curve for later use;
   c. providing an optimization algorithm which automatically changes at least one pre-defined individual instrument parameter so as to optimize at least one signal characteristic of at least one peak in the signal that corresponds to at least one constituent compound in the mixture;
   d. calculating a quantity or concentration of said at least 2 constituent compounds in the mixture by converting their corresponding peak signal level using the mass detector calibration curve.

2. The method of claim 1, wherein the separation instrument is a gas chromatograph.

3. The method of claim 1, wherein the separation instrument is a high performance liquid chromatograph.

4. The method of claim 1, wherein the mass detector is a light scattering instrument.

5. The method of claim 1, wherein the mass detector is a total elemental detector.

6. The method of claim 1, wherein the mass detector is a total carbon detector.

7. The method of claim 1, wherein the mass detector is a total nitrogen detector.

8. The method of claim 1, wherein the mass detector is a total sulfur detector.

9. The method of claim 1, wherein the control parameters in the optimization algorithm include varying the sensitivity gain settings of the mass detector.

10. The method of claim 1, wherein the control parameters in the optimization algorithm include varying the injection volume of the separation instrument.

11. The method of claim 1, wherein the control parameters in the optimization algorithm include varying the mobile phase gradient of a high performance liquid chromatograph.

12. The method of claim 1, wherein the control parameters in the optimization algorithm include varying any combination of the following parameters: a) the sensitivity gain settings of the mass detector; b) the injection volume of the separation instrument; and c) the mobile phase gradient of a high performance liquid chromatograph.

13. The method of claim 1, wherein the optimization algorithm is used to modify the signal characteristics in a subsequent instrument run following the conclusion of signal acquisition in a prior run.

14. The method of claim 1, wherein the optimization algorithm is used to modify the signal characteristics during the instrument run.

* * * * *